(12) United States Patent
Jaing et al.

(10) Patent No.: US 6,493,070 B1
(45) Date of Patent: Dec. 10, 2002

(54) METHOD FOR IN-SITU MONITORING LAYER UNIFORMITY OF SPUTTER COATING BASED ON INTENSITY DISTRIBUTION OF PLASMA SPECTRUM

(75) Inventors: Cheng-Chung Jaing, Hsinchu (TW);
Chuen-Horng Tsai, Hsinchu (TW);
Jyh-Shin Chen, Hsinchu (TW);
Ming-Hwu Cheng, Hsinchu (TW);
Ho-Yen Hsiao, Hsinchu (TW);
Py-Shiun Yeh, Hsinchu (TW);
Jiann-Shiun Kao, Hsinchu (TW)

(73) Assignee: Precision Instrument Development Center, National Science Council, Hsinchu (TW)

( * ) Notice: Subject to any disclaimer, the term of this patent is extended or adjusted under 35 U.S.C. 154(b) by 339 days.

(21) Appl. No.: 09/642,793

(22) Filed: Aug. 22, 2000

(30) Foreign Application Priority Data

Nov. 20, 1999 (TW) ........................................ 88120334 A

(51) Int. Cl.$^7$ ................................................ G01N 21/00
(52) U.S. Cl. ........................ 356/72; 356/600; 356/601; 427/8
(58) Field of Search .......................... 356/72, 600, 601, 356/606; 427/8, 9, 10

(56) References Cited

U.S. PATENT DOCUMENTS

| 3,809,479 A | * | 5/1974 | Whelan et al. | .............. 250/306 |
| 4,859,277 A | | 8/1989 | Barna et al. | ................. 156/626 |
| 4,888,199 A | * | 12/1989 | Felts et al. | ............. 204/192.13 |

* cited by examiner

Primary Examiner—Frank G. Font
Assistant Examiner—Roy M. Punnoose
(74) Attorney, Agent, or Firm—Bacon & Thomas, PLLC

(57) ABSTRACT

This invention discloses an in-situ monitoring method on the layer uniformity of sputter coatings in a vacuum chamber based on deconvolution of measuring plasma emission spectra. The method of the present invention started from an Ar-normalized Sr intensity distribution derived from deconvoluting the plasma spectra by using Abel inversion method, which was considered as the spatial distribution of the sputtering mass of the source target. The thickness profile on the substrate was then calculated with n-th power of cosine law model. It was observed good agreement between the calculated thickness profile based on spectroscopic measurement and experimental observation. The film uniformity for the same sputter conditions can be monitored by comparing in-situ measurement of Ar-normalized Sr intensity distribution with the standard curve, or by directly calculating thickness distribution on the substrates.

13 Claims, 4 Drawing Sheets

METHOD FOR IN-SITU MONITORING LAYER UNIFORMITY OF SPUTTER COATING BASED ON INTENSITY DISTRIBUTION OF PLASMA SPECTRUM

FIELD OF THE INVENTION

The present invention is related to a method for monitoring layer uniformity of sputter coating, and in particular to an in-situ method for monitoring layer uniformity of sputter coating based on intensity distribution of plasma spectrum.

BACKGROUND

Uniformity is a very important requirement in the fabrication of products when thin-film deposition is needed. In almost all practices, film uniformity can only be characterized after an enormous amount of tests and measurement were conducted. Some works on in-situ measurement of film thickness have been reported, but none could resolve thickness distribution.

U.S. Pat. No. 4,859,277 discloses a method for measuring the concentration profile of an active species across the surface of a semiconductor slice in a plasma reactor, so that uniformity of etch and deposition across the surface of the semiconductor slice can be assured. However, the semiconductor slice very often is kept moving in a processing chamber during etching or depositing, and thus measuring the concentration profile of the active species across the surface of the semiconductor slice as taught in the method of U.S. Pat. No. 4,859,277 is difficult to be carried out.

SUMMARY OF THE INVENTION

A primary objective of the present invention is to provide a real-time film uniformity monitoring method for thin-film deposited by sputtering or evaporation.

Another objective of the present invention is to provide a method for adjusting deposition conditions of a thin film deposited by sputtering or evaporation based on a real-time film uniformity monitoring method.

In order to accomplish the objectives of the present invention a first method for in-situ monitoring layer uniformity of sputter coating provided by the present invention comprises the following steps, wherein the sputter coating is deposited on a surface of a substrate inside a reaction chamber having a target opposite to said substrate and a low pressure working gas therein:

a) measuring intensity of plasma emission light along an axis on a surface parallel to said target, wherein said plasma emission light is generated by sputtering said target;

b) splitting said intensity of plasma emission light to obtain an intensity distribution of a predetermined wavelength of an element constituting said target along said axis and an intensity distribution of a wavelength of said working gas adjacent to said predetermined wavelength along said axis;

c) normalizing said intensity distribution of said predetermined wavelength of said element with said intensity distribution of said adjacent wavelength of said working gas to obtain a normalized intensity distribution; and d) comparing said normalized distribution with a standard normalized distribution of an uniform sputter coating obtained according to steps a), b) and c) in advance, so that the layer uniformity of said sputter coating deposited on said surface of said substrate is in-situ monitored, wherein said uniform sputter coating has a desired layer uniformity directly measured by an instrument, and is deposited under sputtering conditions same as those of said sputter coating under in-situ monitoring.

In step c) of the first method of the present invention, said normalizing comprises dividing an intensity of said predetermined wavelength of said element at a position of said axis by an intensity of said adjacent wavelength of said working gas at the same position of said axis.

In the first method of the present invention, said plasma emission light generated by sputtering said target in step a) is cylindrically symmetric on said surface parallel to said target.

A second method for in-situ monitoring layer uniformity of sputter coating based on intensity distribution of plasma spectrum according to the present invention comprises the following steps:

a) measuring intensity of plasma emission light along an axis on a surface parallel to said target, wherein said plasma emission light is generated by sputtering said target;

b) splitting said intensity of plasma emission light to obtain an intensity distribution of a predetermined wavelength of an element constituting said target along said axis and an intensity distribution of a wavelength of said working gas adjacent to said predetermined wavelength along said axis;

c) deconvoluting the two resulting intensity distributions from step b) to obtain an intensity distribution of said predetermined wavelength of said element along a radius of said surface parallel to said target and an intensity distribution of said wavelength of said working gas adjacent to said predetermined wavelength along said radius of said surface parallel to said target, respectively;

d) normalizing said intensity distribution of said predetermined wavelength of said element along said radius with said intensity distribution of said adjacent wavelength of said working gas along said radius to obtain a normalized intensity distribution; and e) comparing said normalized distribution with a standard normalized distribution of an uniform sputter coating obtained according to steps a), b), c) and d) in advance, so that the layer uniformity of said sputter coating deposited on said surface of said substrate is in-situ monitored, wherein said uniform sputter coating has a desired layer uniformity directly measured by an instrument, and is deposited under sputtering conditions same as those of said sputter coating under in-situ monitoring.

A third method for in-situ monitoring layer uniformity of sputter coating based on intensity distribution of plasma spectrum according to the present invention is similar to the second method except step e) is replaced by the following:

e') calculating the layer uniformity of said sputter coating deposited on said surface of said substrate by using the resulting normalized distribution from step d). Preferably, said calculating in step e') is carried out by using the n-th power of cosine law model and the geometric relationship between a substrate and a target.

Said measuring in step a) of the methods of the present invention preferably is carried out by scanning said plasma emission light along said axis on said surface parallel to said target with an optical fiber outside said reaction chamber.

In step d) of the second and third methods of the present invention, said normalizing comprises dividing an intensity of said predetermined wavelength of said element at a value of said radius by an intensity of said adjacent wavelength of said working gas at the same value of said radius.

In step c) of the second and third methods of the present invention, said deconvoluting preferably is carried out by using Abel Inversion, wherein an intensity distribution of a wavelength of a plasma emission light at a radius r on a surface, inten (r), is obtained by the following formula:

$$inten(r) = \frac{1}{\pi} \int_r^R \frac{\frac{d\, Inten(x)}{dx}}{\sqrt{x^2 - r^2}}\, dx$$

wherein r is a variable representing a value of a radius of the plasma emission light on said surface, R is an assumed radius of the plasma emission light on said surface, x is a variable representing a position of x-axis, and Inten (x) is an intensity of said wavelength of said plasma emission light on said surface, wherein said plasma emission light is cylindrically symmetric on said surface.

In the method of the present invention the intensity distribution of plasma spectrum is measured across a surface above the target, so that the method of the present invention is applicable to deposition methods wherein the substrate to be deposited is kept moving in the processing chamber, and particularly the method of the present invention is applicable to deposition methods wherein more than one substrates are to be deposited in the processing chamber.

DETAILED DESCRIPTION OF A PREFERRED EMBODIMENT OF THE INVENTION

The inventors of the present application conducted a simulation work on the layer uniformity of sputter coatings in a vacuum chamber based on both deconvolution of measuring plasma emission spectra and calculation with cosine law (Milton Ohring, "The Materials Science of Thin Films" chap.3, Academic Press INC, 1992; Donald L. Smith, "Thin-Film Deposition principles & Practice", McGraw-Hill INC, 1995). It was then compared to the corresponding measurement of film thickness distribution. Good agreement between simulation and experimental observation revealed that the simulation method based on spectroscopic measurement could be used as an in-situ monitoring of the deposition uniformity.

Figure 1:
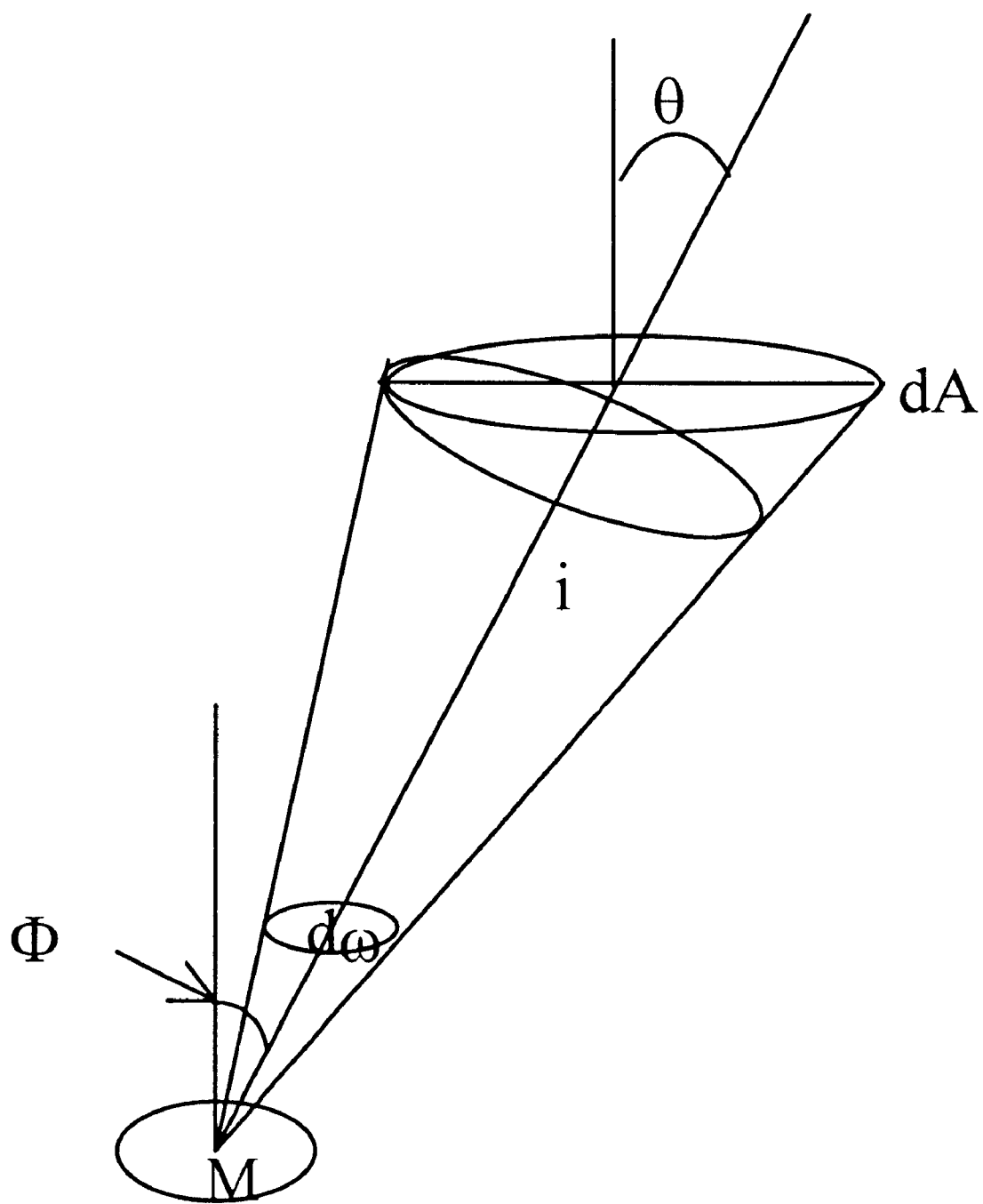
FIG. 1 shows a geometric relationship between the substrate to be deposited and the target in the method of the present invention.

Assuming a target source is a directional plane emitting source, a mass of material emitted from an emitting point of the target source passing through a substrate is proportional to n degree of cosine φ, wherein φ is the emitting angle as shown in FIG. 1. Accordingly, a formula (1) is proposed as follows:

$$dM = \frac{m(n+1)}{2\pi} \cos^n \Phi d\omega = \frac{m(n+1)\cos^n \Phi \cos\theta dA}{2\pi i^2} \quad (1)$$

wherein m is the total mass of material emitted from the target source, dM is the total mass of the emitted material passing through the substrate, dω is the conic angle between the emitting point and the substrate, dA is the area of the substrate, i is the distance between the point of the target source and the substrate, Φ is the emitting angle defined as an angle between a normal line of the target source and a line from the emitting point to a deposited point of the substrate, and θ is the angle between a normal line of the substrate and a line from the emitting point to a deposited point of the substrate. n is the exponent of the cosine law, and is a distribution constant of the deposition process, wherein the distribution thereof becomes narrow as n increases. The total mass of the emitted material passing through the substrate, dM, can be represented by the following formula (2):

$$dM = utdA \quad (2)$$

wherein t is the film thickness on the substrate, and u is the density of the film. From the formulas (1) and (2), we can obtain $$t = \frac{m(n+1)\cos^n \Phi \cos\theta}{2\pi u i^2} \quad (3)$$

Figure 2:
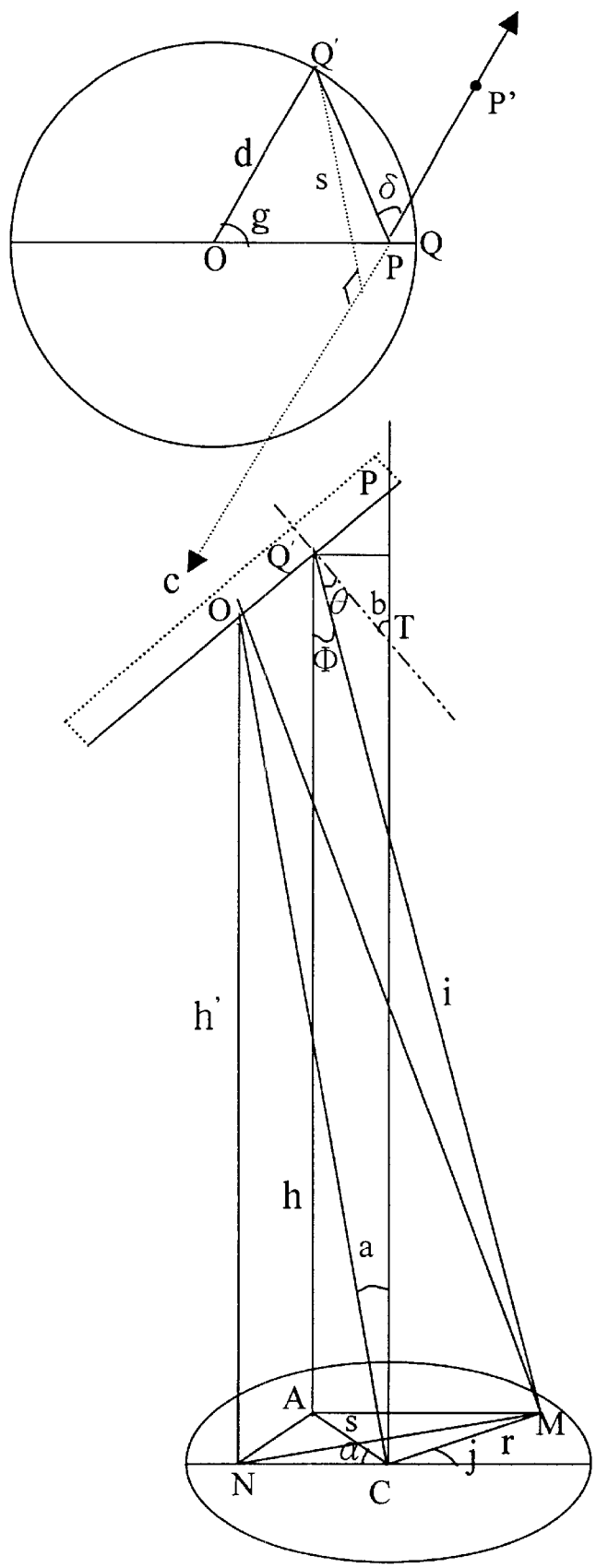
FIG. 2 shows a geometric relationship between the substrate to be deposited and the target in a preferred embodiment according to the method of the present invention.

When the substrate is rotating about the central axis during sputtering process, the film thickness at Q' on the ring of radius d is $$t = \frac{m(n+1)}{4\pi^2 u} \int_0^{2\pi} \frac{\cos^n \Phi \cos\theta}{i^2} \, dg \quad (4)$$

wherein g is an angle of the point Q' on the substrate as shown in FIG. 2.

FIG. 2 shows a geometric relationship between the substrate to be deposited and the target in a preferred embodiment according to the method of the present invention, wherein O represents the center of the substrate, and C represents the center of the target. The normal line at the C on the target intersects the substrate at a point P. The angle between a line CP and a line PQ is 50°. P' is an arbitrary point on the line CP and above the substrate, M is an arbitrary point on the target of radius r and an angle j. A is a point on the target so that the normal line at the point A intersects the point Q' on the substrate. N is a point on the target so that the normal line at the point N intersects the point O on the substrate. The normal line at the Q' on the substrate intersects the line CP at a point T. The following equations stand from the geometry shown in FIG. 2: ∠Q'TP=b=40°; ∠TQ'M=θ; ∠AQ'M=Φ; ∠OCP=a=10°; ∠ACN=α; ∠P'PQ'=δ; $\overline{CO}$=215.8 mm; $\overline{CA}$=s (a distance from the point Q' to $\overline{CP}$); $\overline{AQ'}$=h; $\overline{NO}$=h'; $\overline{Q'M}$=i.

$$h' = \overline{CO} \cos a = 215.8 \cos 10° \quad (5)$$

$$h = h' + d \sin b \cos g \quad (6)$$

$$s = \overline{PQ'} \sin \delta \quad (7)$$

$$\cos\delta = \frac{\overline{PQ'}^2 + \overline{PP'}^2 - \overline{P'Q'}^2}{2\overline{PQ'}\,\overline{PP'}} \qquad (8)$$

$$\overline{PQ'}^2 = \overline{OP}^2 + d^2 - 2d\overline{OP}\cos g \qquad (9)$$

$$\overline{OP} = \overline{co}\sin a \sec b \qquad (10)$$

$$\overline{P'Q'}^2 = (\overline{PP'}\cos b)^2 + (d\sin g)^2 + (\overline{PP'}\sin b + \overline{OP} - d\cos g)^2 \qquad (11)$$

$$i^2 = s^2 = r^2 - 2sr\cos(\pi - j - \alpha) \qquad (12)$$

$$\cos\alpha = \frac{s^2 + \overline{CN}^2 - \overline{AN}^2}{2s\overline{CN}} \qquad (13)$$

$$\overline{CN} = \overline{CO}\sin\alpha \qquad (14)$$

$$\overline{AN} = \sqrt{d^2 - (d\sin\alpha\cos g)^2} \qquad (15)$$

$$\cos\Phi = \frac{h}{i} \qquad (16)$$

$$\cos\theta = \sqrt{1 - \cos^2(90° - \theta)} \qquad (17)$$

$$\cos(90° - \theta) = \frac{d^2 + i^2 - \overline{OM}^2}{2di} \qquad (18)$$

$$\overline{OM} = i_0 \text{ (wherein } i_0 \text{ is the value of } i \text{ when } d=0\text{)} \qquad (19)$$

Let us consider the target source has an area of a circle, and the film thickness on the substrate results from the sputtering of the whole target source. Further, the magnetron plasma on the target is supposed to be symmetrical to the axis of the normal to the sputter gun, resulting in symmetrical sputtering rates on the target. For the same sputtering process, sputtering time is a constant. The distribution of the mass of material sputtered from the target is consistent with the distribution of sputtering rate on the target, so that the mass of material sputtered from the target varies with the radius of the target, i.e. m=m(r). Therefore, the film thickness t represented by equation (4) should be integrated with respect to r and j in FIG. 2, and becomes $$t = \frac{(n+1)}{4\pi^2 u}\int_0^{2\pi}\int_0^{2\pi}\int_0^z \frac{m(r)\cos^n\Phi\cos\theta}{i^2}\,dg\,dj\,dr \qquad (20)$$

wherein z is the radius of the target source.

Therefore, the film thickness on the substrate is thus obtained by substituting equations (5) to (19) into equation (20), if m(r) is known. In the following we will describe the relationship between the intensity distribution of plasma emission light based on spectroscopic measurement (distribution of putter atom concentration) and the distribution of the mass of material sputtered from the target, m(r).

Figure 3:
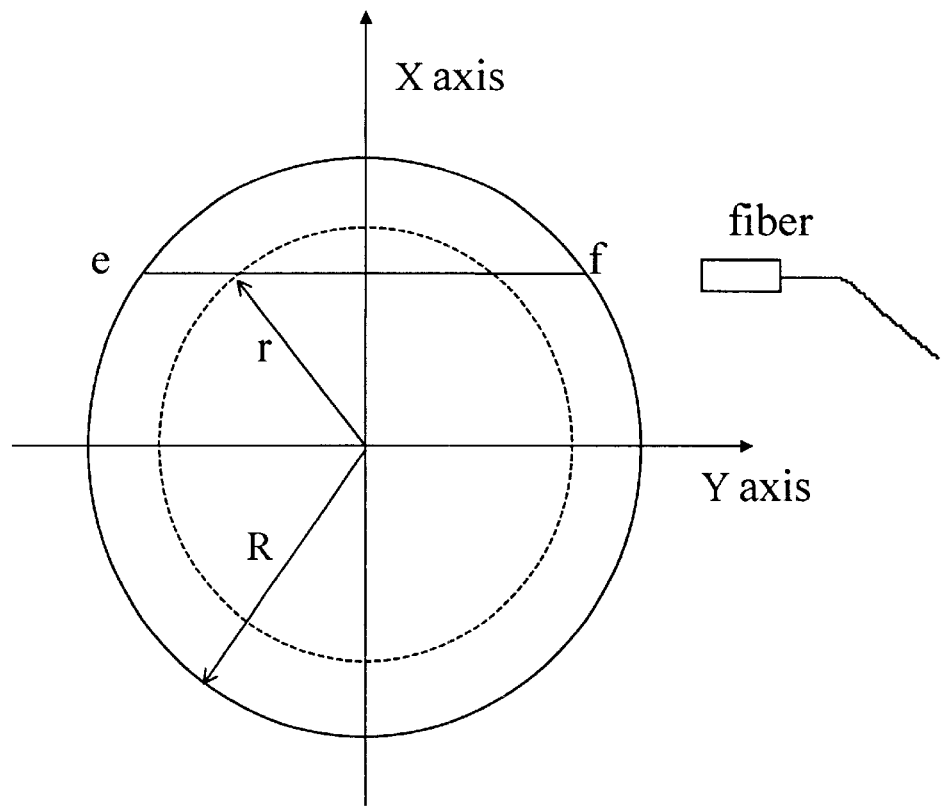
FIG. 3 shows a schematic view of the fiber scanning in the preferred embodiment according to the method of the present invention.

When an optical fiber is installed and scanned along the axis (X-axis) at fixed distance to the target surface, the fiber at each position at x receives the plasma emission light from the chord $\overline{ef}$, as shown in FIG. 3. Inten(x) is the integral of the intensity inten($x^2 + y^2$) of each position of the plasma emission light across the chord $\overline{ef}$, neglecting the self-absorption of plasma.

$$\text{Inten}(x) = \int_{-\sqrt{R^2 x^2}}^{\sqrt{R^2 x^2}} \text{inten}(x^2 + y^2)\,dy$$

wherein R is the assumed plasma core region.

After re-expressing the above equation from X-Y coordinate system to a cylindrical coordinate system, we obtain:

$$\text{Inten}(x) = 2\int_x^R \frac{\text{inten}(r^2)r}{\sqrt{r^2 - x^2}}\,dr \qquad (21)$$

After deconvolution by using Abel Inversion method [W. Lochte-Holtgreven, "Plasma Diagnostics", American Institute of Physics, New York 1 995], the intensity distribution of the plasma light along the radius r, inten(r), is given by:

$$\text{inten}(r) = \frac{1}{\pi}\int_r^R \frac{\frac{d\,\text{Inten}(x)}{dx}}{\sqrt{x^2 - r^2}}\,dx \qquad (22)$$

Assume the integrated intensity Inten(x) can be expressed by a polynomial as:

$$\text{Inten}(x) = coe_a x^{12} + coe_b x^{10} + coe_c x^8 + coe_d x^6 + coe_e x^4 + coe_f x^2 + coe_g \qquad (23)$$

wherein $coe_a$, $coe_b$, $coe_c$, $coe_d$, $coe_e$, $coe_f$, and $coe_g$ are coefficients and can be obtained by best-fitting the data measured by optical spectrometry connected to scanning fiber. Substituting equation (23) into equation (22) we can obtain the intensity distribution of the plasma light along the radius r, inten(r).

Experiments

The vacuum chamber was cryogenically pumped to a base pressure of $1.33 \times 10^{-4}$ Pa. The pure argon working gas was introduced at 40 SCCM (standard cubic centimeter per minute) flow rate controlled with a mass flow controller and the chamber pressure was maintained at 0.9 Pa during the deposition. The vacuum chamber system consisted of dual four-inch sputter guns which were symmetric relative to the normal on the center of the substrate. The diameter of the silicon substrate was 90 mm and the diameter of the target was 100 mm. The radio frequency magnetron sputter gun was used to sputter the $SrTiO_3$ target. For this set of experiments, the r.f. power was maintained at 190 watts. The deposition time was seventy-five minutes. The film thickness was determined by a spectroscopic ellipsometer of company Sopra, France. Optical emission spectra were obtained using a 500 mm monochromator of company ARC (Model SpectroPro-500) equipped with 1200 g/mm grating. The dispersed light was detected with a TE-cooled charge coupled device (CCD-576 EUV) and recorded by a computer with a software CSMA. The spectral response of the monochromator/detector measurement system was determined using the calibrated profiles of grating and detector. The spectral response curve was used to correct all plasma emission spectra that were recorded.

Results and Discussions

Figure 4:
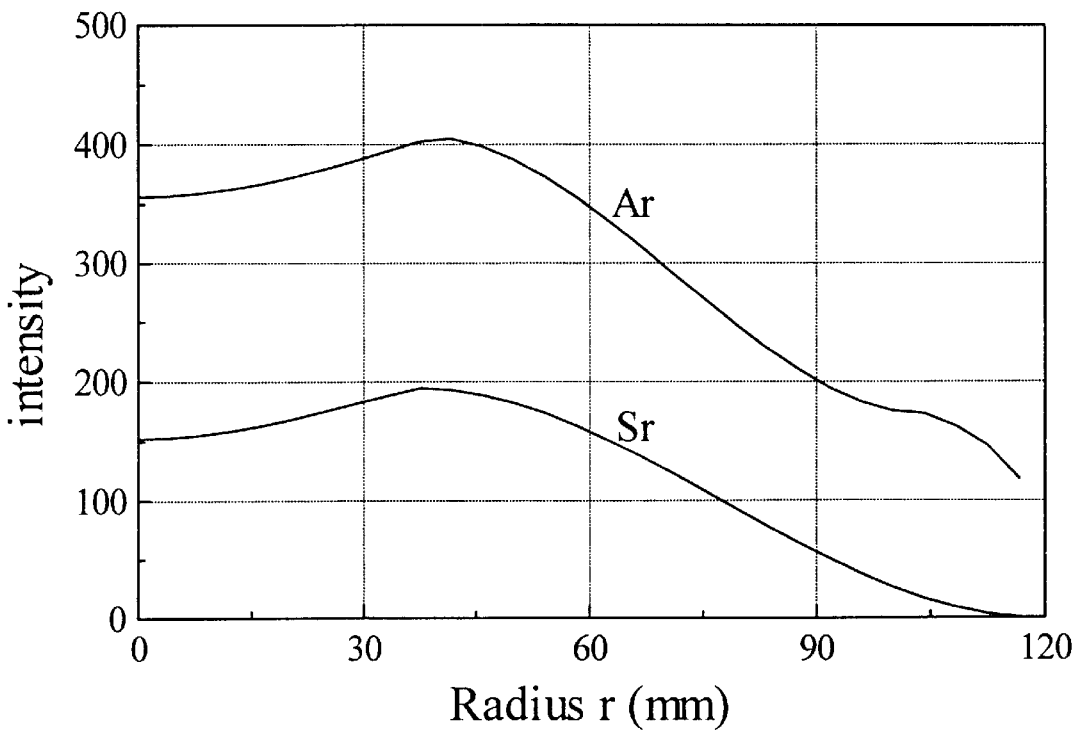
FIG. 4 is an intensity vs. radius plot showing Sr intensity distribution of 640.8 nm and Ar intensity distribution of 675.2 nm for 190 watts power.

FIG. 4 shows Sr intensity distribution of 640.8 nm and Ar intensity distribution of 675.2 nm for 190 watts power measured at a position 15 mm above $SrTiO_3$ target source. These distributions were obtained by splitting the plasma emission light scanned by the optical fiber, detecting intensity distributions of predetermined wavelengths via a detector, recording Inten(x) in a computer, and carrying out calculations of equations (22) and (23) in said computer.

Figure 5:
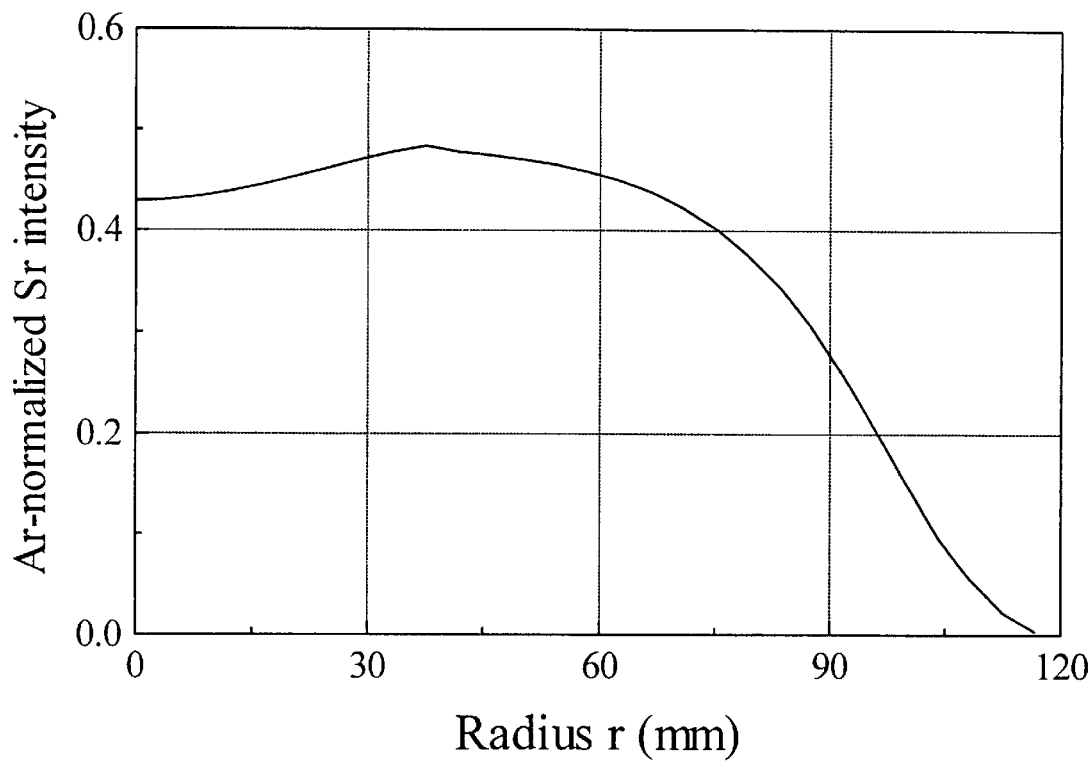
FIG. 5 is a Ar-normalized Sr intensity distribution plot from FIG. 4.

FIG. 5 shows the Ar-normalized Sr intensity distribution of plasma light for the r.f. power 190 watts, in which Sr line of wavelength 640.8 nm and Ar line of wavelength 675.2 nm were chosen. The intensity of the Sr line at 640.8 nm was found reasonably strong to show the variation with varying power. The wavelength of the Ar line at 675.2 nm is close to it of the Sr line at 640.8 nm and the intensity of the Ar line at 675.2 nm was apparent. In deriving FIG. 4, deconvolution from raw spectral data by using Abel inversion method was carried out. The resulting spectral intensity distribution after Abel inversion corresponds to the concentration profile of "excited" sputtered Sr atoms, which varies with the product of the local concentration of sputtered atoms and electron density assuming the excitation is dominated by electron impact. Since electron density is usually orders of magnitude higher than the sputtered atom concentration, the product of the small spatial variation of electron density multiplied by the mean sputtered atom concentration could be considered second order variation compared to the product of the spatial variation of sputtered atom concentration multiplied by the mean electron density. Therefore, the deconvoluted spectral distribution could reasonably be assumed representing the spatial variation of sputtered atom concentration. However, in order to take into account the effect of electron density distribution, the Ar-intensity variation was used to normalize the Sr-intensity assuming ground state Ar concentration was spatially uniform. The result is shown in FIG. 5, which shows that there is a maximum intensity at r=37.5 mm due to magnetic confinement. This is consistent with the observation on the target that an erosion ring track at radius of 37.5 mm was observed. The Ar-normalized Sr intensity of plasma light decreases outside the region of the target and decreases to about zero at r=116.7 mm.

Figure 6:
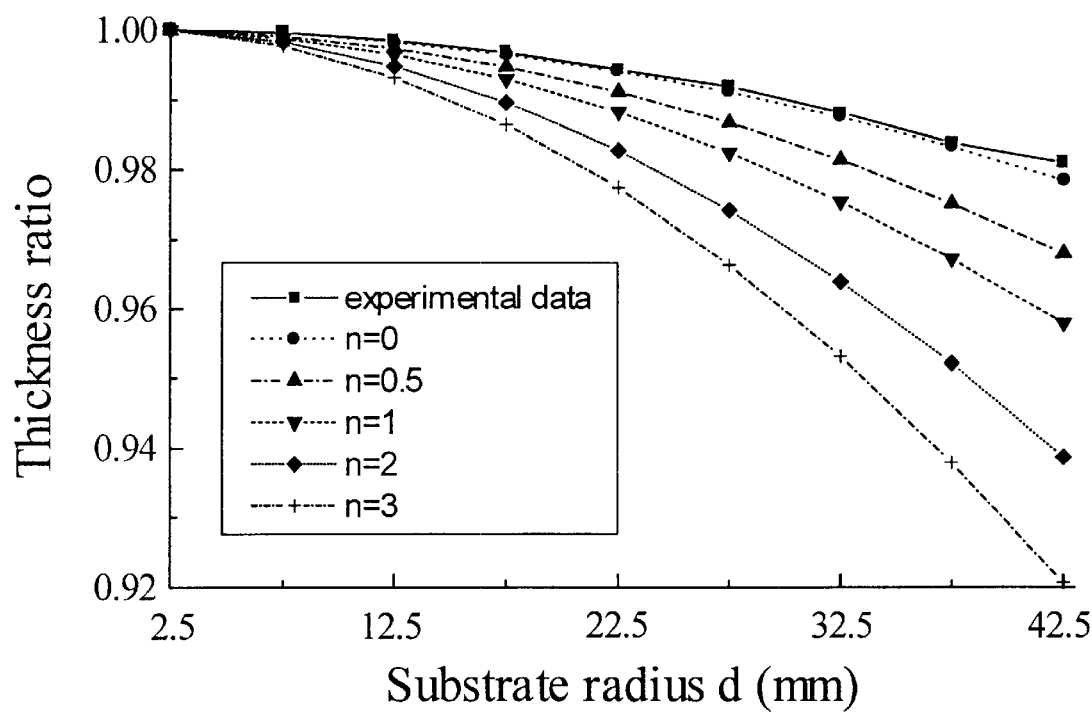
FIG. 6 is a thickness ratio vs. substrate radius plot showing thickness distribution for 190 watts power and various exponents of the cosine law.

FIG. 6 shows the thickness distribution on the substrates for the experiments of the r.f, power 190 watts by using the Ar-normalized Sr intensity distribution of plasma light (FIG. 5) as the distribution of the mass of material sputtered from the target, m(r), along with the simulations of various exponents of the cosine law [equation (20)]. The interval of thickness measurement was 5 mm on the substrate. The film thickness on the center of the substrate was 97.6 nm. Comparing the data of the experiment with that of the simulation, FIG. 6 shows that the exponent of the cosine law is best fitted to be zero (n=0). At the working pressure 0.9 Pa in this experiment, the mean free path of the sputtered atoms was approximately 8 mm, so the atoms should experience more than 20 collisions with Ar gases before they arrived at the substrate. From the spatial distribution points of view, the effect of collisions could be included in the exponent of the cosine law.

Good agreement between simulation and experimental observation revealed that the thickness distribution on the substrate in the sputter deposition can be in-situ predicted based on in-situ measurement of plasma emission spectra and the n-th power of cosine law model. That is the film uniformity for the same sputter conditions can be monitored by comparing in-situ measurement of Ar-normalized Sr intensity distribution along the axis (X-axis) with a standard normalized distribution, or by comparing in-situ measurement of Ar-normalized Sr intensity distribution with the curve shown in FIG. 5, or by calculating thickness distribution on the substrates from equation (20).

What is claimed is:

1. A method for in-situ monitoring layer uniformity of sputter coating based on intensity distribution of plasma spectrum, wherein the sputter coating is deposited on a surface of a substrate inside a reaction chamber having a target opposite to said substrate and a low pressure working gas therein, which comprises the following steps:
   a) measuring intensity of plasma emission light along an axis on a surface parallel to said target, wherein said plasma emission light is generated by sputtering said target;
   b) splitting said intensity of plasma emission light to obtain an intensity distribution of a predetermined wavelength of an element constituting said target along said axis and an intensity distribution of a wavelength of said working gas adjacent to said predetermined wavelength along said axis;
   c) normalizing said intensity distribution of said predetermined wavelength of said element with said intensity distribution of said adjacent wavelength of said working gas to obtain a normalized intensity distribution; and
   d) comparing said normalized distribution with a standard normalized distribution of an uniform sputter coating obtained according to steps a), b) and c) in advance, so that the layer uniformity of said sputter coating deposited on said surface of said substrate is in-situ monitored, wherein said uniform sputter coating has a desired layer uniformity directly measured by an instrument, and is deposited under sputtering conditions same as those of said sputter coating under in-situ monitoring.

2. The method according to claim 1, wherein said normalizing in step c) comprises dividing an intensity of said predetermined wavelength of said element at a position of said axis by an intensity of said adjacent wavelength of said working gas at the same position of said axis.

3. The method according to claim 1, wherein said plasma emission light generated by sputtering said target in step a) is cylindrically symmetric on said surface parallel to said target.

4. The method according to claim 1, wherein said measuring in step a) is carried out by scanning said plasma emission light along said axis on said surface parallel to said target with an optical fiber outside said reaction chamber.

5. A method for in-situ monitoring layer uniformity of sputter coating based on intensity distribution of plasma spectrum, wherein the sputter coating is deposited on a surface of a substrate inside a reaction chamber having a target opposite to said substrate and a low pressure working gas therein, which comprises the following steps:
   a) measuring intensity of plasma emission light along an axis on a surface parallel to said target, wherein said plasma emission light is generated by sputtering said target;
   b) splitting said intensity of plasma emission light to obtain an intensity distribution of a predetermined wavelength of an element constituting said target along said axis and an intensity distribution of a wavelength of said working gas adjacent to said predetermined wavelength along said axis;
   c) deconvoluting the two resulting intensity distributions from step b) to obtain an intensity distribution of said predetermined wavelength of said element along a radius of said surface parallel to said target and an intensity distribution of said wavelength of said working gas adjacent to said predetermined wavelength along said radius of said surface parallel to said target, respectively;
   d) normalizing said intensity distribution of said predetermined wavelength of said element along said radius with said intensity distribution of said adjacent wavelength of said working gas along said radius to obtain a normalized intensity distribution; and e) comparing said normalized distribution with a standard normalized distribution of an uniform sputter coating obtained according to steps a), b), c) and d) in advance, so that the layer uniformity of said sputter coating deposited on said surface of said substrate is in-situ monitored, wherein said uniform sputter coating has a desired layer uniformity directly measured by an instrument, and is deposited under sputtering conditions same as those of said sputter coating under in-situ monitoring.

6. The method according to claim 5, wherein said normalizing in step d) comprises dividing an intensity of said predetermined wavelength of said element at a value of said radius by an intensity of said adjacent wavelength of said working gas at the same value of said radius.

7. The method according to claim 5, wherein said measuring in step a) is carried out by scanning said plasma emission light along said axis on said surface parallel to said target with an optical fiber outside said reaction chamber.

8. The method according to claim 5, wherein said deconvoluting in step c) is carried out by using Abel Inversion, wherein an intensity distribution of a wavelength of a plasma emission light at a radius r on a surface, inten (r), is obtained by the following formula:

$$inten(r) = \frac{1}{\pi} \int_r^R \frac{\frac{d\,Inten(x)}{dx}}{\sqrt{x^2 - r^2}} dx$$

wherein r is a variable representing a value of a radius of the plasma emission light on said surface, R is an assumed radius of the plasma emission light on said surface, x is a variable representing a position of x-axis, and Inten (x) is an intensity of said wavelength of said plasma emission light on said surface, wherein said plasma emission light is cylindrically symmetric on said surface.

9. A method for in-situ monitoring layer uniformity of sputter coating based on intensity distribution of plasma spectrum, wherein the sputter coating is deposited on a surface of a substrate inside a reaction chamber having a target opposite to said substrate and a low pressure working gas therein, which comprises the following steps:

a) measuring intensity of plasma emission light along an axis on a surface parallel to said target, wherein said plasma emission light is generated by sputtering said target;

b) splitting said intensity of plasma emission light to obtain an intensity distribution of a predetermined wavelength of an element constituting said target along said axis and an intensity distribution of a wavelength of said working gas adjacent to said predetermined wavelength along said axis;

c) deconvoluting the two resulting intensity distributions from step b) to obtain an intensity distribution of said predetermined wavelength of said element along a radius of said surface parallel to said target and an intensity distribution of said wavelength of said working gas adjacent to said predetermined wavelength along said radius of said surface parallel to said target, respectively;

d) normalizing said intensity distribution of said predetermined wavelength of said element along said radius with said intensity distribution of said adjacent wavelength of said working gas along said radius to obtain a normalized intensity distribution;

e) calculating the layer uniformity of said sputter coating deposited on said surface of said substrate by using the resulting normalized distribution from step d).

10. The method according to claim 9, wherein said normalizing in step d) comprises dividing an intensity of said predetermined wavelength of said element at a value of said radius by an intensity of said adjacent wavelength of said working gas at the same value of said radius.

11. The method according to claim 9, wherein said measuring in step a) is carried out by scanning said plasma emission light along said axis on said surface parallel to said target with an optical fiber outside said reaction chamber.

12. The method according to claim 9, wherein said deconvoluting in step c) is carried out by using Abel Inversion, wherein an intensity distribution of a wavelength of a plasma emission light at a radius r on a surface, inten (r), is obtained by the following formula:

$$inten(r) = \frac{1}{\pi} \int_r^R \frac{\frac{d\,Inten(x)}{dx}}{\sqrt{x^2 - r^2}} dx$$

wherein r is a variable representing a value of a radius of the plasma emission light on said surface, R is an assumed radius of the plasma emission light on said surface, x is a variable representing a position of x-axis, and Inten (x) is an intensity of said wavelength of said plasma emission light on said surface, wherein said plasma emission light is cylindrically symmetric on said surface.

13. The method according to claim 9, wherein said calculating in step e) is carried out by using the n-th power of cosine law model and the geometric relationship between a substrate and a target.

* * * * *